(12) United States Patent
Heikkilä et al.

(10) Patent No.: US 11,984,202 B2
(45) Date of Patent: May 14, 2024

(54) REMOTE MONITORING OF MEASUREMENTS IN CLINICAL TRIALS (71) Applicant: SIGNANT HEALTH GLOBAL LLC, Blue Bell, PA (US)

(72) Inventors: Antti Heikkilä, Espoo (FI); Riku Lehtomäki, Helsinki (FI)

(73) Assignee: CRF BOX OY, Helsinki (FI)

( * ) Notice: Subject to any disclaimer, the term of this patent is extended or adjusted under 35 U.S.C. 154(b) by 0 days.

(21) Appl. No.: 16/454,261

(22) Filed: Jun. 27, 2019

(65) Prior Publication Data
US 2020/0005909 A1     Jan. 2, 2020

(30) Foreign Application Priority Data
Jun. 29, 2018 (FI) ..................... 20185604

(51) Int. Cl.
*G16H 10/20* (2018.01)
*G16H 10/60* (2018.01)
*G16H 20/10* (2018.01)

(52) U.S. Cl.
CPC ............ *G16H 10/20* (2018.01); *G16H 10/60* (2018.01); *G16H 20/10* (2018.01)

(58) Field of Classification Search
CPC ........ G16H 10/20; G16H 10/60; G16H 20/10; G16H 40/67; G16H 20/00; H04W 76/00; A61B 5/0002

(Continued)

(56) References Cited

U.S. PATENT DOCUMENTS 6,494,831 B1 * 12/2002 Koritzinsky ........... G16H 40/40
                                                              128/903
2006/0047538 A1    3/2006 Condurso et al.
(Continued)

FOREIGN PATENT DOCUMENTS

EP        3264302 A1      1/2018
WO     2007073484 A2      6/2007

OTHER PUBLICATIONS

Finnish Patent and Registration Office, Search Report, Application No. 20185604, dated Oct. 29, 2018, 2 pages.
(Continued)

*Primary Examiner* — Jonathan Ng
*Assistant Examiner* — Benjamin L. Hanks
(74) *Attorney, Agent, or Firm* — HOGAN LOVELLS US LLP (57) ABSTRACT The present disclosure allows remote monitoring of measurements in clinical trials. Clinical trial participant data units received from a client device are accessed. The clinical trial participant data units are set to include a clinical trial diary entry from a clinical trial diary application in the client device and clinical trial measurement samples corresponding to the clinical trial diary entry from a measurement device connected to the client device via a short-range wireless connection. If it is determined that such a data unit lacks any collected clinical trial measurement samples, a wireless connection log is searched for a corresponding connectivity issue entry. If such an entry is found, it is determined that a potential connectivity issue exists and a connectivity correction action is triggered. Otherwise, it is determined that a potential compliance issue exists and a compliance correction action is triggered.

14 Claims, 5 Drawing Sheets (58) Field of Classification Search
USPC .......................................................... 705/2–3
See application file for complete search history.

(56) References Cited

U.S. PATENT DOCUMENTS

| | | | |
|---|---|---|---|
| 2006/0143047 A1 | 6/2006 | Briegs et al. | |
| 2009/0113244 A1* | 4/2009 | Doshi | H04W 24/08 714/25 |
| 2011/0176712 A1 | 7/2011 | Hill et al. | |
| 2011/0252057 A1 | 10/2011 | Huang et al. | |
| 2012/0323796 A1* | 12/2012 | Udani | G16H 10/20 705/80 |
| 2014/0187889 A1 | 7/2014 | Cohen et al. | |
| 2016/0029420 A1* | 1/2016 | Rajan | H04W 76/11 370/329 |

OTHER PUBLICATIONS

Ramkissoon, Charrise M et al—"A review of safety and hazards associated with the artificial pancreas" IEEE Reviews in Biomedical Engineering, vol. 10 pp. 44-62, XP011675441, ISSN: 1937-3333, DOI: 1109/RBME.2017.2749038.

Rolf Kraemer et al—Part I introduction—, Short-range wireless communications: Emerging Technologies and Applications, Jan. 20, 2009, pp. 2-26, XP055638150 URL:https:/pdfs.semanticscholar.org/5527/3af5bc503eec465bcb3b18d110346a8c282e.pdf.

Ana Sasa Bastinos, European Search Report dated Nov. 13, 2019; EP 19 18 2844, Munich.

Anonymous: "Healthcare I Wi-Fi Alliance", Aug. 18, 2017 (Aug. 18, 2017), XP055979076, Retrieved from the Internet: URL:https://web.archive.org/web/20170818091743/https://www.wi-fi.org/discover-wi-fi/healthcare [retrieved on Nov. 8, 2022].

Anonymous: "Short-range device—Wikipedia", Jun. 16, 2018 (Jun. 16, 2018), XP055982956, Retrieved from the Internet: URL:https://en.wikipedia.org/w/index.php?title=Short-range_device&direction=next&oldid=841547053 [retrieved on Nov. 18, 2022].

Anonymous: "ERC Recommendation 70-07 Relating to the use of Short Range Devices (SRO)", Oct. 13, 2017 (Oct. 13, 2017), XP055982950, Retrieved from the Internet: URL:https://docdb.cept.org/download/3490 [retrieved on Nov. 18, 2022].

European Office Action issued in European Application No. 9182844.1 dated Nov. 24, 2022.

\* cited by examiner

FIG. 5

REMOTE MONITORING OF MEASUREMENTS IN CLINICAL TRIALS

BACKGROUND

Field

The present application generally relates to clinical trials. In particular, the present application relates to remote monitoring of measurements in clinical trials.

Description of the Related Art

Nowadays, clinical trials may utilize electronic or digital clinical trial diary (or patient diary) devices. Typically, the electronic clinical trial diary reminds a participant to fill in data (such as answers to validated questionnaires and symptoms occurrences, and/or other information about the participant's condition) at the right time and presents only the questions the participant should answer at that time. In addition, the electronic clinical trial diary may time stamp the recorded data and maintain an audit trail of changes to the data in order to ensure the integrity and validity of the data.

Furthermore, various electronic or digital measurement devices may be distributed to the participants in a clinical trial to enable the participants to collect measurement samples e.g. at home. Such measurement devices include e.g. blood glucose measurement devices, ketone measurement devices, and the like.

These measurement devices may utilize various wireless connection techniques to enable them to connect to the electronic clinical trial diary device, since a wired connection would typically be cumbersome and unpractical.

Typically, the electronic clinical trial diary device collects the diary data and the measurement data, and periodically forwards them to a clinical trial server device or the like for storage. In clinical trials data integrity may require safe storage, and it is possible that data may be edited only after submission of a data clarification form (DCF). The DCF is a questionnaire used in clinical research to clarify possible discrepancies and ask for clarification. The DCF is part of the data validation process in a clinical trial.

However, problems may arise when the participant fills in the diary but no measurement is received, or the participant takes a measurement but there's no corresponding diary entry. The reason for this may be related to the electronic clinical trial diary device, the measurement device, the connection between the two devices, or the participant's lack of compliance to follow the trial protocol.

In device related issues, it is typically up to the participant to connect the clinical trial personnel to inform them of the situation and to request a replacement device. It may take several days or even longer before the participant bothers or is able to do this. During this time, the clinical trial is practically suspended for this specific participant causing loss of valuable information. If the underlying issue is the participant's lack of compliance to follow the trial protocol, such an interruption in providing the clinical trial data may continue until the clinical trial personnel discovers the situation and reminds the participant. Yet, currently it may take several days or even longer before the clinical trial personnel becomes aware of such lack of compliance.

SUMMARY

An embodiment of an apparatus comprises at least one processor and at least one memory comprising computer program code. The at least one memory and the computer program code are configured to, with the at least one processor, cause the apparatus to at least:

access one or more clinical trial participant data units received via a network connection from a client device configured to execute a clinical trial diary application for collecting clinical trial diary entries, said client device connected via a short-range wireless connection to at least one measurement device configured to collect a clinical trial measurement sample and transmit the collected clinical trial measurement sample to the client device, wherein each clinical trial participant data unit is set to include a collected clinical trial diary entry and one or more collected clinical trial measurement samples corresponding to the collected clinical trial diary entry;

in response to detecting that an accessed clinical trial participant data unit lacks one or more of the corresponding collected clinical trial measurement samples, search a connection log for a corresponding connectivity issue entry, said connection log being kept by the client device about the status of each short-range wireless connection between the client device and each of the at least one measurement device and said connection log received via the network connection from the client device; and in response to finding a corresponding connectivity issue entry in the connection log, determine that a potential connectivity issue exists, and cause a connectivity correction action to be triggered.

In an embodiment, alternatively or in addition to the above-described embodiments, the at least one memory and the computer program code are further configured to, with the at least one processor, cause the apparatus to:

in response to not finding a corresponding connectivity issue entry in the connection log, determine that a potential compliance issue exists, and cause a compliance correction action to be triggered.

In an embodiment, alternatively or in addition to the above-described embodiments, the clinical trial participant data unit being set to include a collected clinical trial diary entry and one or more corresponding collected clinical trial measurement samples further comprises the clinical trial participant data unit being set to include a collected clinical trial diary entry and one or more corresponding collected clinical trial measurement samples within a predetermined time window.

In an embodiment, alternatively or in addition to the above-described embodiments, the at least one memory and the computer program code are further configured to, with the at least one processor, cause the apparatus to perform the search of the connection log for the corresponding connectivity issue entry by searching the connection log for the corresponding connectivity issue entry within said predetermined time window.

In an embodiment, alternatively or in addition to the above-described embodiments, the clinical trial diary entries relate to a predetermined activity of a clinical trial participant.

In an embodiment, alternatively or in addition to the above-described embodiments, the predetermined activity of the clinical trial participant comprises at least one of eating or taking an insulin bolus related to a meal, the clinical trial diary entries comprise meal reports, and the corresponding clinical trial measurement samples comprise at least one of blood glucose measurement samples or ketone measurement samples.

In an embodiment, alternatively or in addition to the above-described embodiments, the clinical trial measurement samples comprise clinical trial measurement samples from a continuous clinical trial measurement.

In an embodiment, alternatively or in addition to the above-described embodiments, the connectivity correction action comprises at least one of transmitting an alarm to a technical support entity about the potential connectivity issue or transmitting instructions to the client device for trouble-shooting the potential connectivity issue.

In an embodiment, alternatively or in addition to the above-described embodiments, the compliance correction action comprises at least one of transmitting an alarm to a clinical trial entity about the potential compliance issue, transmitting a reminder to the client device about clinical trial compliance, or transmitting instructions to the client device about correct use of at least one of the client device or the at least one measurement device.

In an embodiment, alternatively or in addition to the above-described embodiments, the short-range wireless connection comprises one of a Bluetooth connection, a near field communication, NFC, based connection, and a Wi-Fi connection.

In an embodiment, alternatively or in addition to the above-described embodiments, the connectivity issue comprises at least one of a pairing issue, empty batteries issue, an end-user related device issue, or a faulty measurement device issue.

An embodiment of a method of remotely monitoring clinical trial measurements comprises:
accessing, by a processor, one or more clinical trial participant data units received via a network connection from a client device configured to execute a clinical trial diary application for collecting clinical trial diary entries, said client device connected via a short-range wireless connection to at least one measurement device configured to collect a clinical trial measurement sample and transmit the collected clinical trial measurement sample to the client device, wherein each clinical trial participant data unit is set to include a collected clinical trial diary entry and one or more collected clinical trial measurement samples corresponding to the collected clinical trial diary entry;
in response to detecting, by the processor, that an accessed clinical trial participant data unit lacks one or more of the corresponding collected clinical trial measurement samples:
  searching, by the processor, a connection log for a corresponding connectivity issue entry, said connection log being kept by the client device about the status of each short-range wireless connection between the client device and each of the at least one measurement device and said connection log received via the network connection from the client device; and
  in response to finding, by the processor, a corresponding connectivity issue entry in the connection log:
    determining, by the processor, that a potential connectivity issue exists; and
    causing, by the processor, a connectivity correction action to be triggered.

In an embodiment, alternatively or in addition to the above-described embodiments, the method further comprises:
in response to not finding, by the processor, a corresponding connectivity issue entry in the connection log:
  determining, by the processor, that a potential compliance issue exists; and
  causing, by the processor, a compliance correction action to be triggered.

In an embodiment, alternatively or in addition to the above-described embodiments, the clinical trial participant data unit being set to include a collected clinical trial diary entry and one or more corresponding collected clinical trial measurement samples further comprises the clinical trial participant data unit being set to include a collected clinical trial diary entry and one or more corresponding collected clinical trial measurement samples within a predetermined time window.

In an embodiment, alternatively or in addition to the above-described embodiments, the searching of the connection log for the corresponding connectivity issue entry further comprises searching the connection log for the corresponding connectivity issue entry within said predetermined time window.

In an embodiment, alternatively or in addition to the above-described embodiments, the clinical trial diary entries relate to a predetermined activity of a clinical trial participant.

In an embodiment, alternatively or in addition to the above-described embodiments, the predetermined activity of the clinical trial participant comprises at least one of eating or taking an insulin bolus related to a meal, the clinical trial diary entries comprise meal reports, and the corresponding clinical trial measurement samples comprise at least one of blood glucose measurement samples or ketone measurement samples.

In an embodiment, alternatively or in addition to the above-described embodiments, the clinical trial measurement samples comprise clinical trial measurement samples from a continuous clinical trial measurement.

In an embodiment, alternatively or in addition to the above-described embodiments, the connectivity correction action comprises at least one of transmitting an alarm to a technical support entity about the potential connectivity issue or transmitting instructions to the client device for trouble-shooting the potential connectivity issue.

In an embodiment, alternatively or in addition to the above-described embodiments, the compliance correction action comprises at least one of transmitting an alarm to a clinical trial entity about the potential compliance issue, transmitting a reminder to the client device about clinical trial compliance, or transmitting instructions to the client device about correct use of at least one of the client device or the at least one measurement device.

An embodiment of a computer program product comprises at least one computer-readable storage medium, the computer-readable storage medium comprising a set of instructions, which, when executed by one or more processors, cause an apparatus to at least perform:
accessing one or more clinical trial participant data units received via a network connection from a client device configured to execute a clinical trial diary application for collecting clinical trial diary entries, said client device connected via a short-range wireless connection to at least one measurement device configured to collect a clinical trial measurement sample and transmit the collected clinical trial measurement sample to the client device, wherein each clinical trial participant data unit is set to include a collected clinical trial diary entry and one or more collected clinical trial measurement samples corresponding to the collected clinical trial diary entry;
in response to detecting that an accessed clinical trial participant data unit lacks one or more of the corresponding collected clinical trial measurement samples:
  searching a connection log for a corresponding connectivity issue entry, said connection log being kept by the client device about the status of each short-range wireless connection between the client device and each of the at least one measurement device and said connection log received via the network connection from the client device; and in response to finding, a corresponding connectivity issue entry in the connection log:

determining that a potential connectivity issue exists; and
causing a connectivity correction action to be triggered.

An embodiment of a system comprises:

a client device configured to execute a clinical trial diary application for collecting clinical trial diary entries;

at least one measurement device connected to the client device via a short-range wireless connection, and configured to collect a clinical trial measurement sample and transmit the collected clinical trial measurement sample to the client device, wherein a collected clinical trial diary entry and one or more collected clinical trial measurement samples corresponding to the collected clinical trial diary entry are set to constitute a clinical trial participant data unit; and the apparatus according to any of the above embodiments, wherein the client device is further configured to keep a connection log about the status of each short-range wireless connection between the client device and each of the at least one measurement device, and transmit the clinical trial participant data units and the connection logs via a network connection to the apparatus or to a network device accessible by the apparatus.

At least some of the embodiments allow remote monitoring of measurements in clinical trials, thus making it possible to quickly detect when there are problems in receiving clinical trial participant data.

Furthermore, at least some of the embodiments allow quickly determining whether the underlying issue relates to device errors, non-compliance or user errors (such as incorrect use of the devices).

Furthermore, at least some of the embodiments allow notifying a suitable party or parties associated with the clinical trial (e.g. technical support staff or the like) when device errors are detected, so that they can provide a fix or a new device.

Furthermore, at least some of the embodiments allow notifying a suitable party among the clinical trial personnel (e.g. a nurse or the like) when non-compliance is detected, so that they can contact the participant to improve compliance.

BRIEF DESCRIPTION OF THE DRAWINGS

The accompanying drawings, which are included to provide a further understanding of the present disclosure and constitute a part of this specification, illustrate embodiments of the present disclosure and together with the description help to explain the principles of the present disclosure. In the drawings.

Like reference numerals are used to designate like parts in the accompanying drawings.

DETAILED

Reference will now be made in detail to embodiments of the present disclosure, examples of which are illustrated in the accompanying drawings. The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Figure 1:
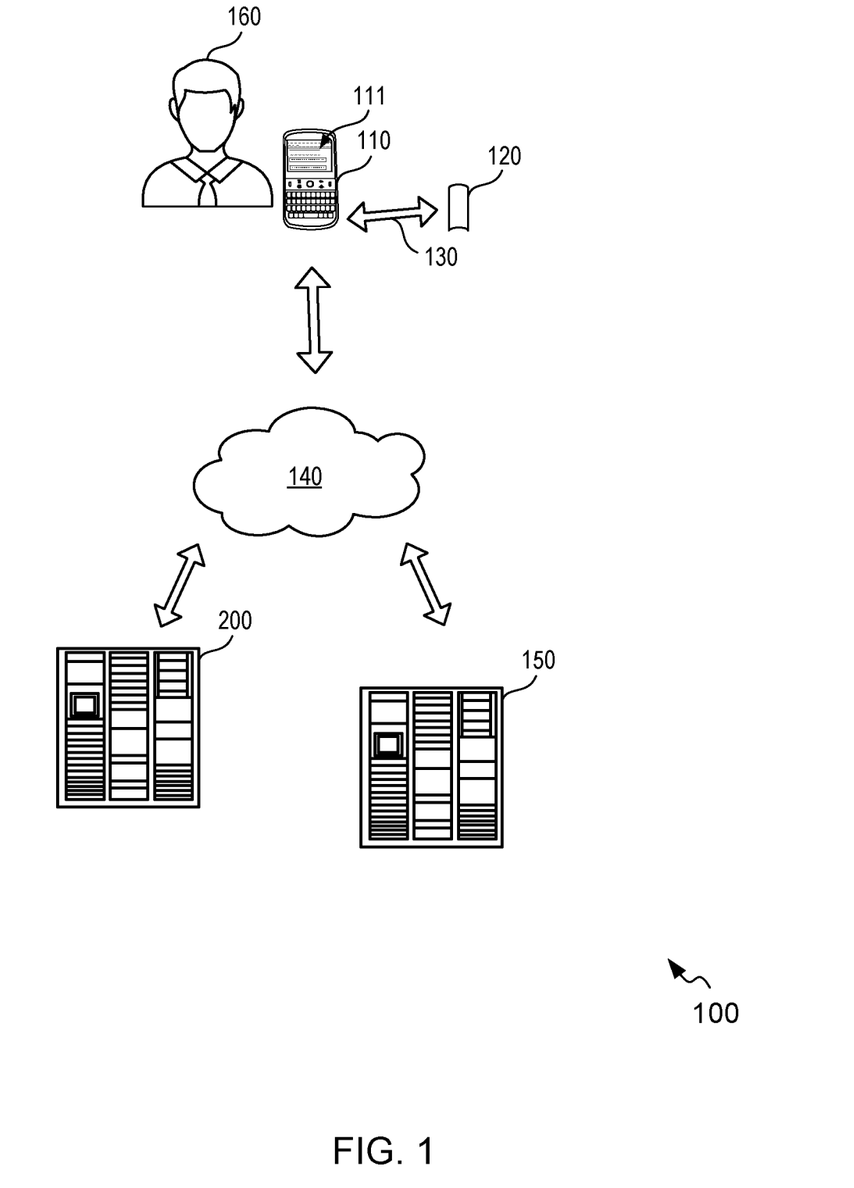
FIG. 1 illustrates an example system, where various embodiments of the present disclosure may be implemented.

FIG. 1 illustrates an example system 100, where various embodiments of the present disclosure may be implemented. An example representation of the system 100 is shown depicting a network 140 that connects entities such as a clinical trial participant 160 with a client device 110, an apparatus 200, as well as a network device 150 accessible by the apparatus 200. The apparatus 200 and/or the network device 150 may comprise a clinical trial server (or server cluster) used to e.g. manage clinical trials. The network 140 may be a centralized network or it may comprise a plurality of sub-networks that may offer a direct communication between the entities or may offer indirect communication between the entities. Examples of the network 140 include wireless networks, wired networks, and combinations thereof. Some non-exhaustive examples of wireless networks may include wireless local area networks (WLANs), cellular networks and the like. Some non-exhaustive examples of wired networks may include Local Area Networks (LANs), Ethernet, Fiber Optic networks and the like. An example of a combination of wired networks and wireless networks may include the Internet.

The client device 110 is configured to execute the clinical trial diary application 111 for collecting clinical trial diary entries. The client device 110 may include e.g. a mobile phone, a smartphone, a tablet computer, a smart watch, or any hand-held or portable device having capability to run a clinical trial diary application. In an embodiment, the clinical trial diary entries include meal reports. The meal reports (or any other clinical trial diary entries) may be entered manually by the participant, or e.g. by scanning a barcode (that comprises data suitable for the meal report, such as the amount of carbohydrates) or the like on groceries packaging. Even though FIG. 1 shows the clinical trial diary application 111 deployed in the client device 110, the clinical trial diary application 111 may alternatively be deployed on another device (such as a network server or the like) in which case the client device 110 may execute the clinical trial diary application 111 remotely, e.g. via a suitable web-based interface.

The client device 110 is connected via a short-range wireless connection 130 to at least one measurement device 120 that is configured to collect clinical trial measurement samples. Examples of the measurement device 120 include e.g. blood glucose measurement devices, ketone measurement devices, spirometers, activity and sleep monitors, wearable health monitoring devices, or any suitable measurement device the data of which can be used to complement participant-entered data. In an embodiment, the measurement device 120 includes a measurement device capable of continuous clinical trial measurements, such as continuous heart rate measurements, continuous blood pressure measurements, continuous oxygen saturation measurements, continuous body temperature measurements, continuous blood glucose measurements, continuous accelerometer measurements, continuous electrocardiogram (ECG) measurements, and/or continuous electroencephalogram (EEG) measurements. The measurement device 120 may be powered by one or more batteries. The batteries may be rechargeable or disposable. Also, the measurement device 120 itself may be disposable (e.g. to be replaced when its batteries are run down).

The short-range wireless connection 130 may comprise e.g. any of the following: a Bluetooth connection, a near field communication (NFC) based connection, and a Wi-Fi (or wireless local area network, WLAN) connection. The communication between the client device 110 and the at least one measurement device 120 may be based on a proprietary communication protocol or an open communication protocol.

The apparatus 200 may be used to store and run an application (or applications) for remotely monitoring clinical trial measurements in accordance with the embodiments presented herein. Examples of the apparatus 200 include, but are not limited to, a desktop computer, a laptop computer, a network server running a service, and/or a network terminal.

Figure 2:
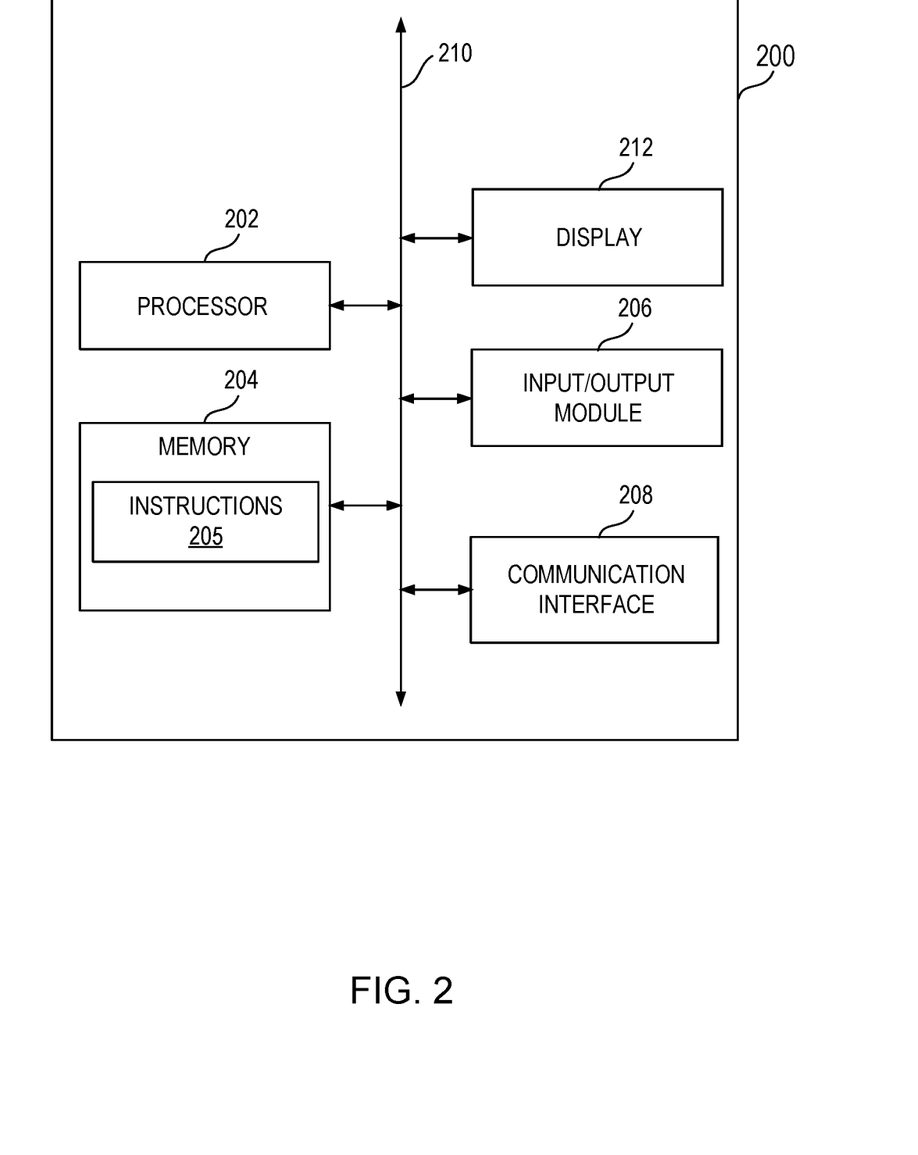
FIG. 2 is a block diagram of an apparatus configured to remotely monitor clinical trial measurements, in accordance with an example embodiment.

FIG. 2 is a block diagram of an apparatus 200 that is configured to remotely monitor clinical trial measurements, in accordance with an example embodiment.

The apparatus 200 comprises one or more processors 202, and one or more memories 204 that comprise computer program code 205. The apparatus 200 may also include a display 212, an input/output module 206, and/or a communication interface 208.

Although the apparatus 200 is depicted to include only one processor 202, the apparatus 200 may include more processors. In an embodiment, the memory 204 is capable of storing instructions 205 (e.g. an operating system and/ various applications). Furthermore, the processor 202 is capable of executing the stored instructions 205. In an embodiment, the processor 202 may be embodied as a multi-core processor, a single core processor, or a combination of one or more multi-core processors and one or more single core processors. For example, the processor 202 may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like. In an embodiment, the processor 202 may be configured to execute hard-coded functionality. In an embodiment, the processor 202 is embodied as an executor of software instructions, wherein the instructions may specifically configure the processor 202 to perform the algorithms and/or operations described herein when the instructions are executed.

The memory 204 may be embodied as one or more volatile memory devices, one or more non-volatile memory devices, and/or a combination of one or more volatile memory devices and non-volatile memory devices. For example, the memory 204 may be embodied as semiconductor memories (such as mask ROM, PROM (programmable ROM), EPROM (erasable PROM), flash ROM, RAM (random access memory), etc.).

The input/output module (hereinafter referred to as 'I/O module') 206 is configured to facilitate provisioning of an output and/or receiving an input. The I/O module 206 is configured to be in communication with the processor 202 and the memory 204. Examples of the I/O module 206 include, but are not limited to, an input interface and/or an output interface. Examples of the input interface may include, but are not limited to, a keypad, a touch screen, soft keys, a microphone, and the like. Examples of the output interface may include, but are not limited to, a display such as a light emitting diode display, a thin-film transistor (TFT) display, a liquid crystal display, an active-matrix organic light-emitting diode (AMOLED) display, a microphone, a speaker, and the like. In an example embodiment, the processor 202 may include I/O circuitry configured to control at least some functions of one or more elements of the I/O module 206, such as, for example, a speaker, a microphone, a display, and/or the like. The processor 202 and/or the I/O circuitry may be configured to control one or more functions of the one or more elements of the I/O module 206 through computer program instructions, for example, software and/or firmware, stored on a memory, for example, the memory 204, and/or the like, accessible to the processor 202.

In an embodiment, the I/O module 206 may be configured to provide a user interface (UI) configured to provide options or any other display to a user of the apparatus 200. In addition, the I/O module 206 may be integrated with mechanisms configured to receive inputs from the user of the apparatus 200.

The communication interface 208 may enable the apparatus 200 to communicate with other devices. In an embodiment, various components of the apparatus 200, such as the processor 202, the memory 204, the I/O module 206 and the communication interface 208 are configured to communicate with each other via or through a centralized circuit 210. The centralized circuit 210 may be various devices configured to, among other things, provide or enable communication between the components (202-208 and 212) of the apparatus 200. In certain embodiments, the centralized circuit 210 may be a central printed circuit board (PCB) such as a motherboard, a main board, an electronic device board, or a logic board. The centralized circuit 210 may also, or alternatively, include other printed circuit assemblies (PCAs) or communication channel media.

The apparatus 200 as illustrated and hereinafter described is merely illustrative of an apparatus that could benefit from embodiments of the invention and, therefore, should not be taken to limit the scope of the invention. It is noted that the apparatus 200 may include fewer or more components than those depicted in FIG. 2.

The one or more memories 204 and the computer program code 205 are configured to, with the one or more processors 202, cause the apparatus 200 to access one or more clinical trial participant data units received via a network connection 140 from the client device 110. As discussed above, the client device 110 is a device that is configured to execute the clinical trial diary application 111 (remotely or locally) for collecting clinical trial diary entries. The client device 110 may send the clinical trial participant data units to the apparatus 200. Alternatively, the client device 110 may send the clinical trial participant data units to a network device 150 that is accessible by the apparatus 200.

As discussed above, the client device 110 is connected via the short-range wireless connection 130 to the at least one measurement device 120 that is configured to collect a clinical trial measurement sample. Furthermore, the at least one measurement device 120 is configured to transmit the collected clinical trial measurement samples to the client device 110. The clinical trial measurement samples may be transmitted to the client device 110 e.g. as they are being collected or periodically in batches. Herein, each clinical trial participant data unit is set to include a collected clinical trial diary entry and one or more collected clinical trial measurement samples corresponding to the collected clinical trial diary entry. Herein, the correspondence between the clinical trial measurement samples and the clinical trial diary entries may be e.g. a temporal one. That is, the clinical trial measurement samples corresponding to the clinical trial diary entries may include e.g. clinical trial measurement samples collected within a given time period or time window (such as an hour, several hours, a day, or the like) from the clinical trial diary entries. In other words, each clinical trial participant data unit is intended to include a collected clinical trial diary entry and one or more corresponding (e.g. within a given time period or window as mentioned above) collected clinical trial measurement samples, but due to e.g. connectivity issues or compliance issues this may not always be the case in practice, as will be discussed in more detail below.

The clinical trial diary entries may relate to e.g. a predetermined activity of a clinical trial participant. In an example embodiment, the predetermined activity may comprise eating and/or taking an insulin bolus related to a meal, the clinical trial diary entries may comprise meal reports, and the corresponding clinical trial measurement samples may comprise blood glucose measurement samples and/or ketone measurement samples. In another example embodiment, the predetermined activity may comprise waking up in the morning, the clinical trial diary entry may comprise a morning diary, and the corresponding clinical trial measurement samples may comprise peak expiratory flow (PEF) measurements.

In an example embodiment, the clinical trial measurement samples may comprise clinical trial measurement samples from a continuous clinical trial measurement. In this embodiment, information about when the participant attached the measurement device(s) 120 to himself/herself may be included with the measurement sample(s).

When it is detected that an accessed clinical trial participant data unit lacks one or more of the corresponding collected clinical trial measurement samples, the one or more memories 204 and the computer program code 205 are configured to, with the one or more processors 202, cause the apparatus 200 to search a connection log for a corresponding connectivity issue entry. Again, the correspondence may refer e.g. to the above-described time window or time period. The connection log is kept by the client device 110 about the status of each short-range wireless connection 130 between the client device 110 and each of the at least one measurement device 120. Also, the connection log is received via the network connection 140 from the client device 110 (e.g. periodically or in response to requesting it from the client device 110). The client device 110 may send the connection log to the apparatus 200. Alternatively, the client device 110 may send the connection log to a network device 150 that is accessible by the apparatus 200. The connectivity issue may comprise e.g. any of the following: a pairing issue or the like between the client device 110 and the measurement device 120, empty batteries in the measurement device 120 issue, an end-user related device issue (e.g. device-out-of-range issue, no-measurements-to-transfer issue, device-in-incorrect-state issue, or the like), or a faulty measurement device 120 issue.

When a corresponding connectivity issue entry is found in the connection log, the one or more memories 204 and the computer program code 205 are configured to, with the one or more processors 202, cause the apparatus 200 to determine that a potential connectivity issue exists and cause a connectivity correction action to be triggered. The connectivity correction action may comprise e.g. transmitting an alarm to a technical support entity (e.g. technical support staff or the like) about the potential connectivity issue and/or transmitting instructions to the client device for troubleshooting the potential connectivity issue. For example, a technical support person may be presented with a list of participants with faulty measurement devices 120. Further, this technical support person may be presented with e.g. means (such as a button or the like on a graphical user interface) to order or otherwise obtain replacement measurement devices 120.

When a corresponding connectivity issue entry is not found in the connection log, the one or more memories 204 and the computer program code 205 are configured to, with the one or more processors 202, cause the apparatus 200 to determine that a potential compliance issue exists and cause a compliance correction action to be triggered. The compliance correction action may comprise e.g. transmitting an alarm to a clinical trial entity (e.g. a nurse or the like) about the potential compliance issue, transmitting a reminder to the client device 110 about clinical trial compliance, and/or transmitting instructions to the client device 110 about correct use of the client device 110 and/or the measurement device(s) 120. For example, a nurse or the like may be presented with a list of participants with compliance issues and their telephone numbers or other contact means to allow the nurse to call up participants in question and remind them about the clinical trial compliance. Herein, 'compliance' refers to a participant's compliance with given requirements of clinical trial protocol and/or good clinical trial practice, including e.g. compliance with requirements about when and how to take the clinical trial measurement samples, and when and how to enter the clinical trial diary entries.

Figure 3:
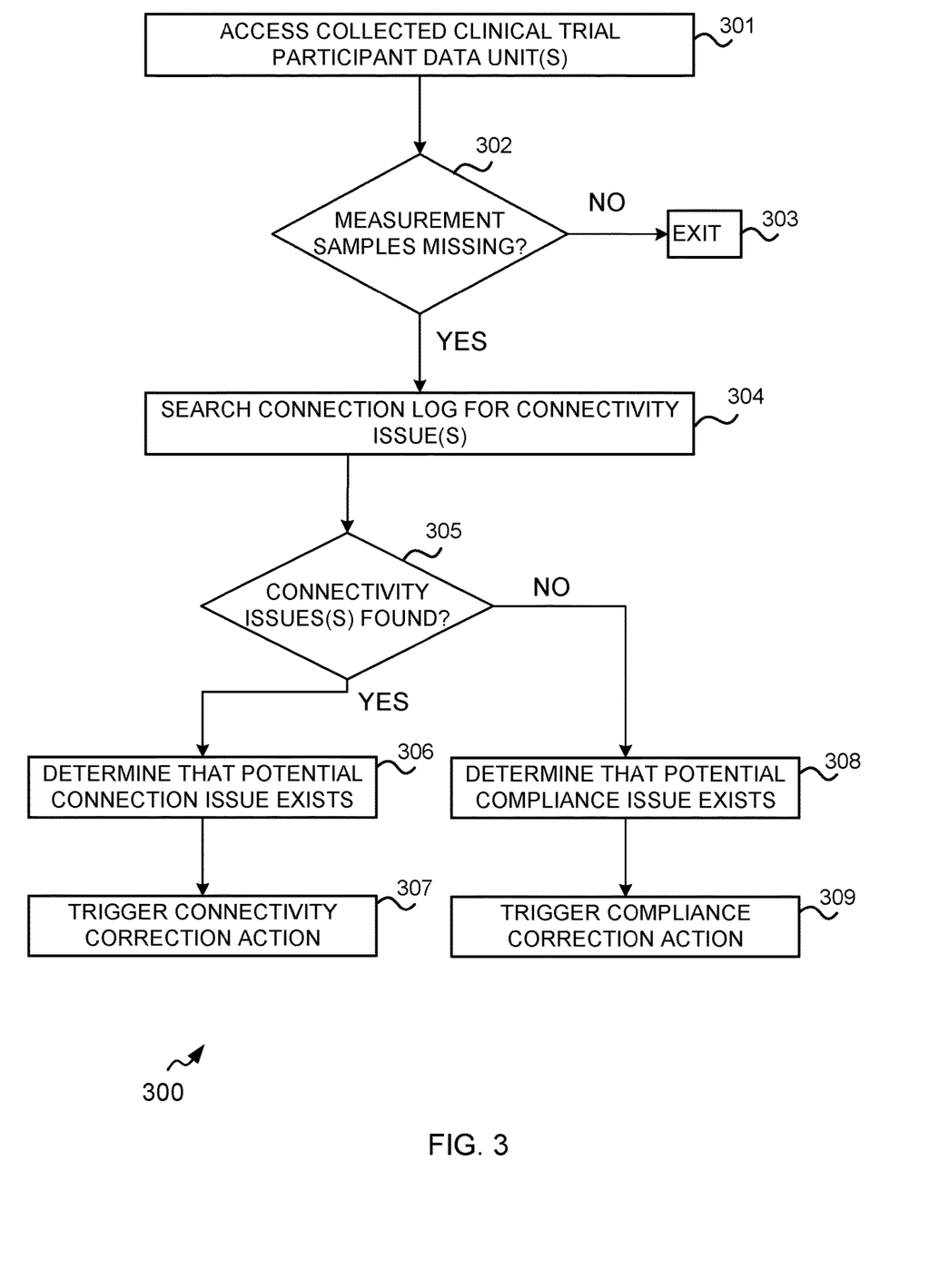
FIG. 3 illustrates an example flow diagram of a method of remotely monitoring clinical trial measurements, in accordance with an example embodiment.

FIG. 3 illustrates an example flow diagram of a method 300 of remotely monitoring clinical trial measurements, in accordance with an example embodiment.

At operation 301, one or more clinical trial participant data units received via a network connection from a client device are accessed by a processor. Herein, the client device is configured to execute a clinical trial diary application for collecting clinical trial diary entries. Furthermore, the client device is connected via a short-range wireless connection to at least one measurement device that is configured to collect a clinical trial measurement sample.

Furthermore, the at least one measurement device is configured to transmit the collected clinical trial measurement samples to the client device over the short-range wireless connection. Herein, each clinical trial participant data unit is set to include a collected clinical trial diary entry and one or more collected clinical trial measurement samples corresponding to the collected clinical trial diary entry. Herein, the correspondence between the clinical trial measurement samples and the clinical trial diary entries may be e.g. a temporal one. That is, the clinical trial measurement samples corresponding to the clinical trial diary entries may include e.g. clinical trial measurement samples collected within a given time window (for example, an hour, four hours, a day, or the like) from the clinical trial diary entries.

The clinical trial diary entries may relate to e.g. a predetermined activity of a clinical trial participant. In an example, the predetermined activity may comprise eating and/or taking an insulin bolus related to a meal, the clinical trial diary entries may comprise meal reports, and the corresponding clinical trial measurement samples may comprise blood glucose measurement samples and/or ketone measurement samples. in an embodiment, at least some of the clinical trial measurement samples may comprise clinical trial measurement samples from a continuous clinical trial measurement If, at operation 302, the processor detects that an accessed clinical trial participant data unit lacks one or more of the corresponding collected clinical trial measurement samples that were set to be included in this clinical trial participant data unit, the method 300 proceeds to operation 304. Otherwise, the method 300 exits, operation 303.

At operation 304, the processor searches a connection log for a connectivity issue entry that corresponds with the clinical trial participant data unit of the missing clinical trial measurement sample(s). Herein, the correspondence may refer e.g. to the above-described time window. Herein, the connection log is kept by the client device and it concerns the status of each short-range wireless connection between the client device and each of the at least one measurement device. Furthermore, the connection log is received via the network connection from the client device.

If, at operation 305, the processor finds a corresponding connectivity issue entry in the connection log, the method proceeds to operation 306.

At operation 306, the processor determines that a potential connectivity issue exists. At operation 307, the processor causes a connectivity correction action to be triggered. The connectivity correction action may comprise e.g. transmitting an alarm to a technical support entity about the potential connectivity issue and/or transmitting instructions to the client device for trouble-shooting the potential connectivity issue.

If, at operation 305, the processor does not find a corresponding connectivity issue entry in the connection log, the method proceeds to operation 308.

At operation 308, the processor determines that a potential compliance issue exists. At operation 309, the processor causes a compliance correction action to be triggered. The compliance correction action may comprise e.g. transmitting an alarm to a clinical trial entity about the potential compliance issue, transmitting a reminder to the client device about clinical trial compliance, and/or transmitting instructions to the client device about correct use of at least one of the client device or the at least one measurement device (e.g. if there is a connection between the measurement device and the client device but there is no reading, the participant may be alerted with instructions such as "Please place the device correctly" or the like).

The method 300 may be performed by the apparatus 200 of FIGS. 1 and 2. Further features of the method 300 directly result from the functionalities and parameters of the apparatus 200 and thus are not repeated here. The method 300 can be performed by computer program(s).

Figure 4:
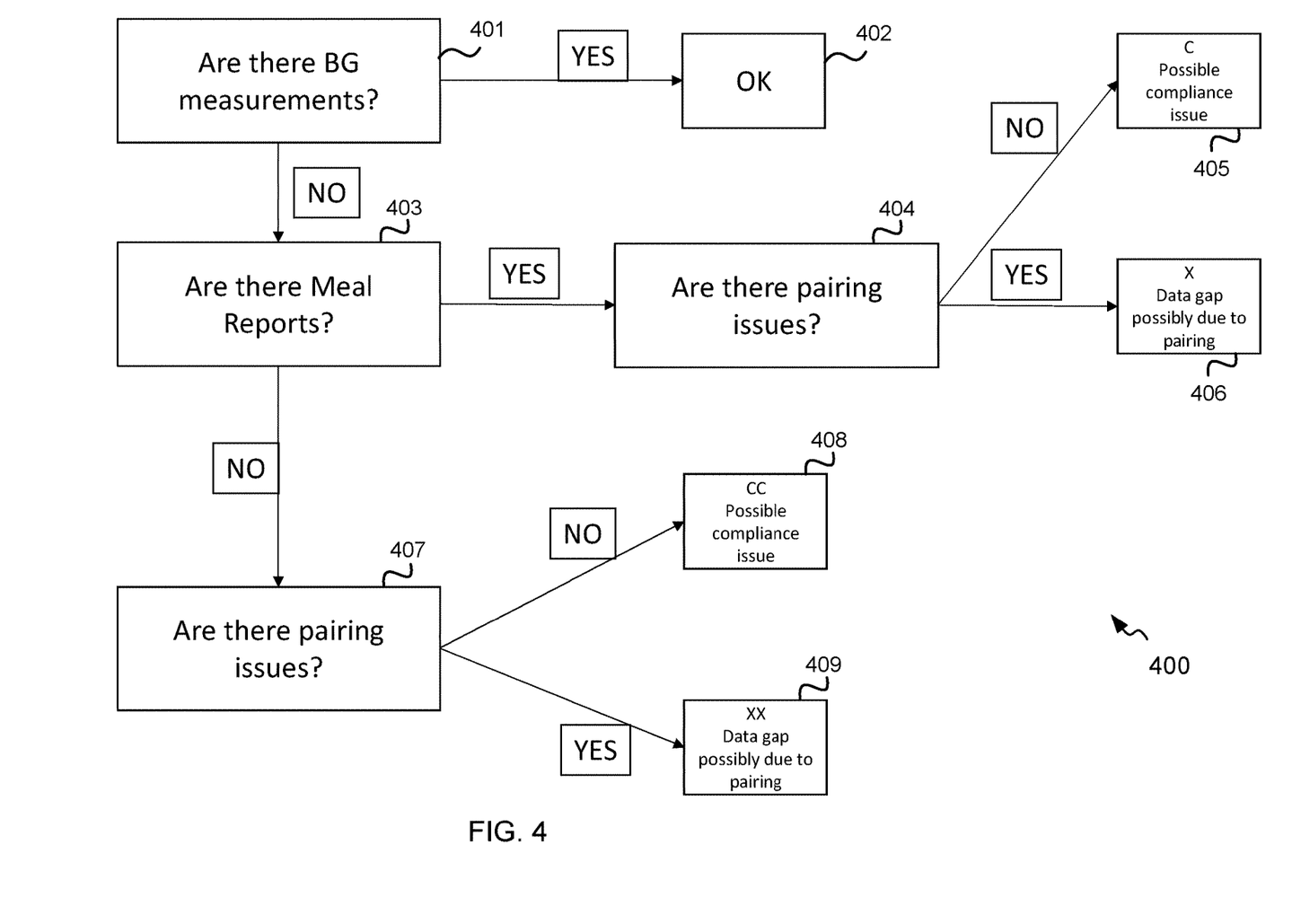
FIG. 4 illustrates an example flow diagram of another method of remotely monitoring clinical trial measurements, in accordance with an example embodiment.

FIG. 4 illustrates an example flow diagram of another method of remotely monitoring clinical trial measurements, in accordance with an example embodiment. At operation 401, it is determined whether blood glucose measurements have been received. If yes, it is determined that there are no issues and the method exits, operation 402.

If no blood glucose measurements have been received, it is determined whether meal reports have been received, operation 403.

If meal reports have been received, it is determined whether there are pairing issues indicated in the connection log, operation 404. If yes, a potential connectivity issue (causing a gap in the collected clinical trial participant data units) is determined, operation 406. If not, a potential compliance issue is determined, operation 405.

If meal reports have not been received, it is determined whether there are pairing issues indicated in the connection log, operation 407. If yes, a potential connectivity issue (causing a gap in the collected clinical trial participant data units) is determined, operation 409. If not, a potential compliance issue is determined, operation 408.

Figure 5:
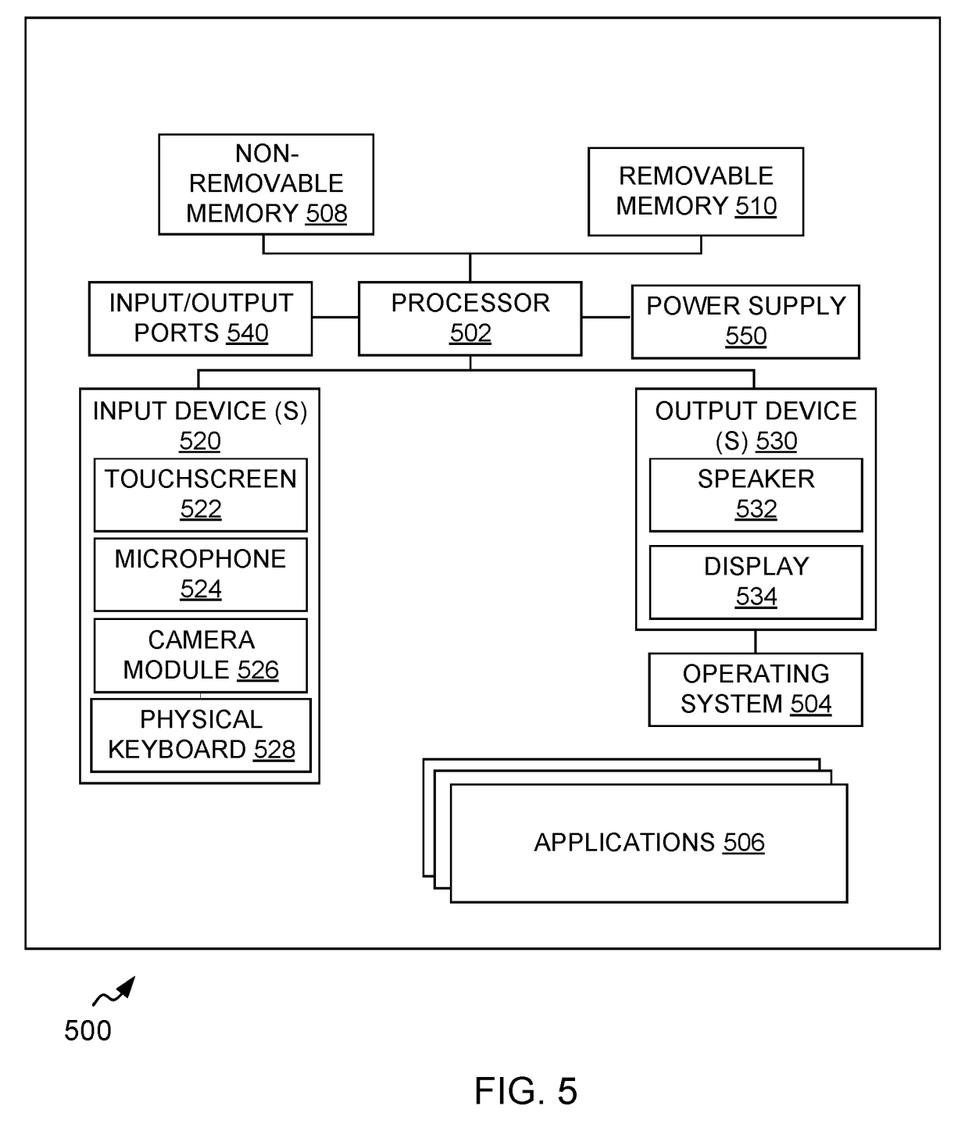
FIG. 5 illustrates an example of an electronic device capable of implementing example embodiments described herein.

FIG. 5 further illustrates an example of an electronic device 500 capable of implementing example embodiments of the client device 110 described herein. It should be understood that the electronic device 500 as illustrated and hereinafter described is merely illustrative of one type of electronic apparatus or device and should not be taken to limit the scope of the embodiments. As such, it should be appreciated that at least some of the components described below in connection with the electronic device 500 may be optional and thus in an example embodiment may include more, less or different components than those described in connection with the example embodiment of FIG. 5. As such, among other examples, the electronic device 500 could be any suitable hand-held computer device, such as smart phone, a tablet computer, or the like.

The illustrated electronic device 500 includes a controller or a processor 502 (i.e. a signal processor, microprocessor, ASIC, or other control and processing logic circuitry) for performing such tasks as signal coding, data processing, input/output processing, power control, and/or other functions. An operating system 504 controls the allocation and usage of the components of the electronic device 500 and support for one or more application programs 506. The application programs 506 can include applications related to clinical trial diaries, or any other applications.

The illustrated electronic device 500 includes one or more memory components, for example, a non-removable memory 508 and/or removable memory 510. The non-removable memory 508 may include RAM, ROM, flash memory, a hard disk, or other well-known memory storage technologies. The removable memory 510 may include flash memory (such as one or more removable flash drives) or smart cards. The one or more memory components may be used for storing data and/or code for running the operating system 504 and the applications 506. Example of data may include text, images, sound files, image data, video data, or other data sets to be sent to and/or received from one or more network servers or other devices via one or more wired or wireless networks.

The electronic device 500 can support one or more input devices 520 and one or more output devices 530. Examples of the input devices 520 may include, but are not limited to, a touchscreen 522 (i.e., capable of capturing finger tap inputs, finger gesture inputs, multi-finger tap inputs, multi-finger gesture inputs, or keystroke inputs from a virtual keyboard or keypad), a microphone 524 (i.e., capable of capturing voice input), a camera module 526 (i.e., capable of capturing still picture images and/or video images) and a physical keyboard 528. Examples of the output devices 530 may include, but are not limited to a speaker 532 and a display 534. Other possible output devices (not shown) can include piezoelectric or other haptic output devices. Some devices can serve more than one input/output function. For example, the touchscreen 522 and the display 534 can be combined into a single input/output device.

The electronic device 500 can further include one or more input/output ports 540, and a power supply 550. The illustrated components are not required or all-inclusive, as any of the components shown can be deleted and other components can be added.

The exemplary embodiments can include, for example, any suitable computer devices and the like, capable of performing the processes of the exemplary embodiments. The devices and subsystems of the exemplary embodiments can communicate with each other using any suitable protocol and can be implemented using one or more programmed computer systems or devices.

One or more interface mechanisms can be used with the exemplary embodiments, including, for example, Internet access, telecommunications in any suitable form (e.g., voice, modem, and the like), wireless communications media, and the like. For example, employed communications networks or links can include one or more satellite communications networks, wireless communications networks, cellular communications networks, 3G communications networks, 4G communications networks, Public Switched Telephone Network (PSTNs), Packet Data Networks (PDNs), the Internet, intranets, a combination thereof, and the like.

It is to be understood that the exemplary embodiments are for exemplary purposes, as many variations of the specific hardware used to implement the exemplary embodiments are possible, as will be appreciated by those skilled in the hardware and/or software art(s). For example, the functionality of one or more of the components of the exemplary embodiments can be implemented via one or more hardware and/or software devices.

The exemplary embodiments can store information relating to various processes described herein. This information can be stored in one or more memories, such as a hard disk, optical disk, magneto-optical disk, RAM, and the like. One or more databases can store the information used to implement the exemplary embodiments of the present inventions. The databases can be organized using data structures (e.g., records, tables, arrays, fields, graphs, trees, lists, and the like) included in one or more memories or storage devices listed herein. The processes described with respect to the exemplary embodiments can include appropriate data structures for storing data collected and/or generated by the processes of the devices and subsystems of the exemplary embodiments in one or more databases.

All or a portion of the exemplary embodiments can be conveniently implemented using one or more general purpose processors, microprocessors, digital signal processors, micro-controllers, and the like, programmed according to the teachings of the exemplary embodiments of the present inventions, as will be appreciated by those skilled in the computer and/or software art(s). Appropriate software can be readily prepared by programmers of ordinary skill based on the teachings of the exemplary embodiments, as will be appreciated by those skilled in the software art. In addition, the exemplary embodiments can be implemented by the preparation of application-specific integrated circuits or by interconnecting an appropriate network of conventional component circuits, as will be appreciated by those skilled in the electrical art(s). Thus, the exemplary embodiments are not limited to any specific combination of hardware and/or software.

Stored on any one or on a combination of computer readable media, the exemplary embodiments of the present inventions can include software for controlling the components of the exemplary embodiments, for driving the components of the exemplary embodiments, for enabling the components of the exemplary embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the exemplary embodiments of the present inventions can include any suitable interpretable or executable code mechanism, including but not limited to scripts, interpretable programs, dynamic link libraries (DLLs), Java classes and applets, complete executable programs, Common Passenger Request Broker Architecture (CORBA) passengers, and the like. Moreover, parts of the processing of the exemplary embodiments of the present inventions can be distributed for better performance, reliability, cost, and the like.

As stated above, the components of the exemplary embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, and the like. Non-volatile media can include, for example, optical or magnetic disks, magneto-optical disks, and the like. Volatile media can include dynamic memories, and the like. Common forms of computer-readable media can include, for example, a floppy disk, a flexible disk, hard disk, or any other suitable medium from which a computer can read.

While the present inventions have been de-scribed in connection with a number of exemplary embodiments, and implementations, the present inventions are not so limited, but rather cover various modifications, and equivalent arrangements, which fall within the purview of prospective claims.

The invention claimed is:

1. An apparatus, comprising:
  at least one processor;
  a network device comprising a server cluster, wherein the network device stores a clinical trial diary application;
  at least one memory comprising computer program code, wherein at least one memory and the computer program code being configured to, with the at least one processor, cause the apparatus to at least:
  access, by the processor, one or more clinical trial participant data units received via a network connection from a client device configured to execute the clinical trial diary application for collecting clinical trial diary entries via a web-based interface, said client device connected via a short-range wireless connection to at least one measurement device configured to collect continuous clinical trial measurement samples and transmit the collected clinical trial measurement samples to the client device over the short-range wireless connection, wherein each clinical trial participant data unit is set to include a collected clinical trial diary entry and one or more collected clinical trial measurement samples corresponding to the collected clinical trial diary entry;
  determine, by the processor, that at least one of the accessed one or more clinical trial participant data units is missing at least one clinical trial measurement sample;

perform, by the processor, a search of a connection log for a corresponding connectivity issue entry corresponding to the at least one of the accessed one or more clinical trial participant data units missing the at least one clinical trial measurement sample, said connection log stored at the client device and including status of at least the short-range wireless connection between the client device and the at least one measurement device, said connection log received by the apparatus periodically, via the network connection from the client device;

perform, by the processor and based at least in part on the search of the connection log, a connectivity correction action or a compliance correction action, wherein the connectivity correction action comprises at least one of transmitting an alarm to a technical support entity or transmitting instructions to the client device;

and the compliance correction action comprises, in part, changing the orientation of the client device based on a signal from a controller of the client device; and in response to completing the connectivity correction action or the compliance correction action, transmitting at least the at least one missing clinical trial measurement sample from the measurement device to the client device.

2. The apparatus according to claim 1, wherein the clinical trial participant data unit being set to include a collected clinical trial diary entry and one or more corresponding collected clinical trial measurement samples further comprises the clinical trial participant data unit being set to include a collected clinical trial diary entry and one or more corresponding collected clinical trial measurement samples within a predetermined time window.

3. The apparatus according to claim 1, wherein the clinical trial diary entries relate to a predetermined activity of a clinical trial participant.

4. The apparatus according to claim 3, wherein the predetermined activity of the clinical trial participant comprises at least one of eating or taking an insulin bolus related to a meal, the clinical trial diary entries comprise meal reports, and the corresponding clinical trial measurement samples comprise at least one of blood glucose measurement samples or ketone measurement samples.

5. The apparatus according to claim 1, wherein the compliance correction action comprises at least one of transmitting an alarm to a clinical trial entity about the potential compliance issue, transmitting a reminder to the client device about clinical trial compliance, or transmitting instructions to the client device about correct use of at least one of the client device or the at least one measurement device.

6. The apparatus according to claim 1, wherein the short-range wireless connection comprises one of a Bluetooth connection, a near field communication, NFC, based connection, and a Wi-Fi connection.

7. The apparatus according to claim 1, wherein the connectivity issue comprises at least one of an empty batteries issue, an end-user related device issue, or a faulty measurement device issue.

8. The apparatus according to claim 1,
wherein the at least one measurement device includes at least one of a blood glucose measurement device, a ketone measurement device, a spirometer, an activity monitor, a wearable health monitoring device, a heart rate monitoring device, a blood pressure monitoring device, an oxygen saturation measurement device, a body temperate measurement device, an accelerometer measurement device, an electrocardiogram measurement device or an electroencephalogram measurement device.

9. A method of remotely monitoring clinical trial measurements, wherein comprising:
accessing, by a processor, one or more clinical trial participant data units received via a network connection from a client device configured to execute a clinical trial diary application for collecting clinical trial diary entries via a web-based interface, said client device connected via a short-range wireless connection to at least one measurement device configured to collect continuous clinical trial measurement samples and transmit the collected clinical trial measurement samples to the client device over the short-range wireless connection, wherein each clinical trial participant data unit is set to include a collected clinical trial diary entry and one or more collected clinical trial measurement samples corresponding to the collected clinical trial diary entry;

determining, by the processor, that at least one of the accessed one or more clinical trial participant data units is missing at least one clinical trial measurement sample;

performing, by the processor, a search of a connection log for a connectivity issue entry corresponding to the at least one of the accessed one or more clinical trial participant data units missing the at least one clinical trial measurement sample, said connection log stored in the client device and including the status of the short-range wireless connection between the client device and the at least one measurement device, said connection log received periodically, via the network connection from the client device;

performing, by the processor and based at least in part on the search of the connection log, a connectivity correction action or a compliance correction action, wherein the connectivity correction action comprises at least one of transmitting an alarm to a technical support entity or transmitting instructions to the client device;

and the compliance correction action comprises, in part, changing the orientation of the client device based on a signal from a controller of the client device; and in response to completing the connectivity correction action or the compliance correction action, transmitting at least the at least one missing clinical trial measurement sample from the measurement device to the client device.

10. The method according to claim 9, wherein the clinical trial participant data unit being set to include a collected clinical trial diary entry and one or more corresponding collected clinical trial measurement samples further comprises the clinical trial participant data unit being set to include a collected clinical trial diary entry and one or more corresponding collected clinical trial measurement samples within a predetermined time window.

11. The method according to claim 9, wherein the clinical trial diary entries relate to a predetermined activity of a clinical trial participant.

12. The method according to claim 11, wherein the predetermined activity of the clinical trial participant comprises at least one of eating or taking an insulin bolus related to a meal, the clinical trial diary entries comprise meal reports, and the corresponding clinical trial measurement samples comprise at least one of blood glucose measurement samples or ketone measurement samples.

13. The method according to claim 9, wherein the compliance correction action comprises at least one of transmitting an alarm to a clinical trial entity about the potential compliance issue, transmitting a reminder to the client device about clinical trial compliance, or transmitting instructions to the client device about correct use of at least one of the client device or the at least one measurement device.

14. A computer program product comprising at least one non-transitory computer-readable storage medium, wherein the non-transitory computer-readable storage medium comprising a set of instructions, which, when executed by one or more processors, cause an apparatus to at least perform:

accessing, by the one or more processors, one or more clinical trial participant data units received via a network connection from a client device configured to execute a clinical trial diary application for collecting clinical trial diary entries via a web-based interface, said client device connected via a short-range wireless connection to at least one measurement device configured to collect continuous clinical trial measurement samples and transmit the collected clinical trial measurement samples to the client device over the short-range wireless connection, wherein each clinical trial participant data unit is set to include a collected clinical trial diary entry and one or more collected clinical trial measurement samples corresponding to the collected clinical trial diary entry;

determining, by the one or more processors, that at least one of the accessed one or more clinical trial participant data units is missing at least one clinical trial measurement sample;

performing, with the one or more processors, a search of a connection log for a connectivity issue entry corresponding to the at least one of the accessed one or more clinical trial participant data units missing the at least one clinical trial measurement sample, said connection log stored by the client device and including the status of the short-range wireless connection between the client device and the at least one measurement device, said connection log received by the apparatus periodically via the network connection from the client device;

performing, by the one or more processors and based at least in part on the search of the connection log, a connectivity correction action or a compliance correction action wherein the connectivity correction action comprises at least one of transmitting an alarm to a technical support entity or transmitting instructions to the client device;

and the compliance correction action comprises, in part, changing the orientation of the client device based on a signal from a controller of the client device; and in response to completing the connectivity correction action or the compliance correction action, transmitting at least the at least one missing clinical trial measurement sample from the measurement device to the client device.

* * * * *